United States Patent [19]

Cronin

[11] Patent Number: 5,064,418
[45] Date of Patent: Nov. 12, 1991

[54] FILTER MEANS FOR USE WITH SYRINGE AND NEEDLE

[75] Inventor: James J. Cronin, Mission Viejo, Calif.

[73] Assignee: Microgon, Inc., Laguna Hills, Calif.

[21] Appl. No.: 506,546

[22] Filed: Apr. 4, 1990

Related U.S. Application Data

[63] Continuation of Ser. No. 860,104, May 6, 1986, abandoned, which is a continuation-in-part of Ser. No. 762,259, Aug. 5, 1985, abandoned.

[51] Int. Cl.⁵ .............................................. A61M 5/00
[52] U.S. Cl. ..................................................... 604/190
[58] Field of Search ............................... 604/190, 187

[56] References Cited

U.S. PATENT DOCUMENTS

| | | | |
|---|---|---|---|
| 4,014,797 | 3/1977 | Raines et al. | 604/190 X |
| 4,267,053 | 5/1981 | Hashino et al. | 604/190 X |
| 4,453,927 | 6/1984 | Sinko | 604/190 X |

Primary Examiner—John D. Yasko
Attorney, Agent, or Firm—Paul R. Wylie

[57] ABSTRACT

According to this invention, there is provided a filter device adapted to be used with a syringe and a needle wherein longitudinally positioned hollow filter fibres and a flow blocking material are arranged within the tubular body for directing flow through the material of the hollow fibres. The device according to the invention can be embodied either as a single filter element or as a combination syringe, filter and needle.

2 Claims, 3 Drawing Sheets

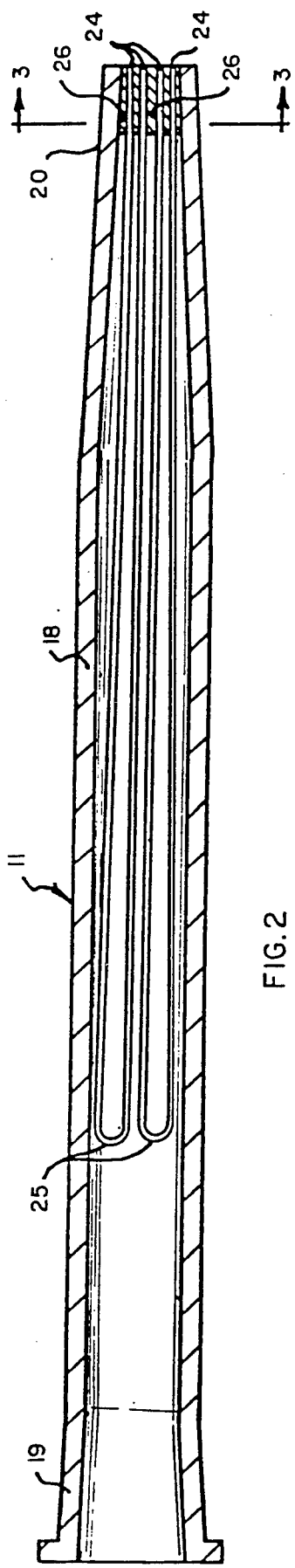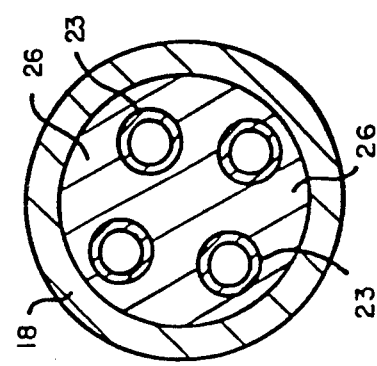

FILTER MEANS FOR USE WITH SYRINGE AND NEEDLE

This is a continuation of copending application Ser. No 06/860,104, filed on May 6, 1986, now abandoned, which is a continuation-in-part of Ser. No. 06/762,259, filed on Aug. 5, 1985, now abandoned.

BACKGROUND OF THE INVENTION

This invention relates generally to a filtering device adapted to be used with a syringe and a needle; and, in another embodiment of the invention, to a combination syringe, needle and filter.

The current state of the art of syringe filters is believed to involve the use of a round flat sheet microporous membrane that is sealed between two plastic halves as an intermediate filter typically for use between a syringe and needle. If air is introduced to the syringe side of one of these filters and pressure is applied, the air is compressed over the entire surface area of the membrane thus substantially blocking or minimizing the flow of fluid. It will be appreciated, that if liquid is introduced to the syringe side of the flat filter (which is horizontal to the vertical axis of the syringe and needle), the liquid will only cover the entire surface of the membrane, in most cases, if the syringe and needle are in a vertical position. If the syringe and needle are in a horizontal position, or angled, the liquid may only cover part of the surface of the membrane thus causing air blockage. Moreover, increased filtering capacity of such filters can only be attained by increasing the diameter resulting in filters having dimensions that sometimes exceed the diameters of the syringe barrels to which they are attached and result in awkward handling.

In recent years, attempts to devise various syringe filters have resulted in that shown in U.S. Pat. No. 4,316,462 which discloses an adapter which extends between the needle that is already in place on the syringe and a second needle. A flat membrane filter is used in this adapter.

According to this invention, there is provided a filtering device adapted to be used with a syringe and a needle wherein longitudinally positioned hollow filter fibres and a flow blocking material are arranged within the tubular body for directing flow through the material of the hollow fibres. The device according to the invention can be embodied either as a single filter element or as a combination syringe, filter and needle.

The foregoing arrangement produces the advantage that, even though the syringe and needle are tipped from vertical during use, the fluid will pass through the filter fibers tangentially to the longitudinal axis of the filter, thus eliminating air blockage. If air is present, any air blockage that will occur will be minimal compared to the flat membrane filters.

SUMMARY OF THE INVENTION

According to this invention, there has been provided a filtering device adapted to be used with a syringe and needle including an elongate tubular body having a first mounting means on the end thereof adapted to be sealingly connected to the needle mounting on said syringe and a second mounting means on the opposite end thereof adapted to be sealingly connected to the cooperative syringe mounting means on said needle. Elongate microporous hollow filter fibres are arranged within said tubular body with said fibres being closed at one end thereof and open at the opposite thereof. A flow blocking material is arranged around said fibres blocking flow through said tubular body other than through the material of the hollow fibres.

In accordance with another aspect of the invention, there is provided a combination syringe, needle and filter utilizing a filter of the foregoing type between the syringe and the needle.

It was an object of this invention to provide a filter for a syringe and needle whereby the fluid drawn into the syringe through the needle or ejected from the syringe through the needle was filtered by a filter means intermediate the syringe and needle.

A further object of this invention was to provide a filter of the foregoing type which would eliminate or minimize air blockage.

A still further object of this invention was to provide a filter for use with a syringe and needle that would be easy to manufacturer and convenient to use.

These and other objects of the invention will be evident from the following more detailed description of the invention.

DESCRIPTION OF THE DRAWINGS

The invention will be more fully understood and described with reference to the drawings wherein:

FIG. 2 is a cross-sectional view of the filter according to the invention;

FIG. 3 is a view in cross-section taken on lines 3—3 of FIG. 2;

DETAILED DESCRIPTION OF THE INVENTION

Figure 1:
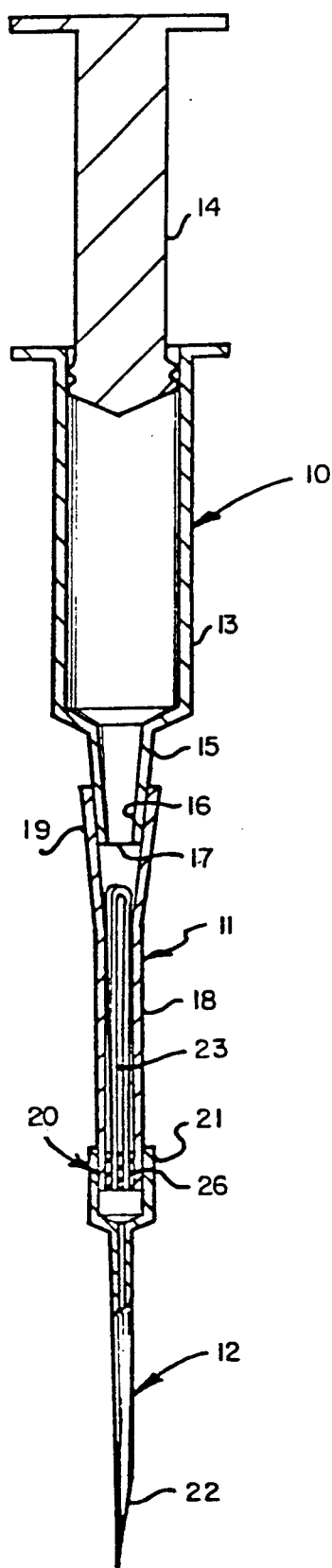
FIG. 1 is a view in cross-section of a syringe, needle and filter according to the invention.

There is shown in FIG. 1 an arrangement according to the invention including a syringe 10, a filter 11 and a needle 12. The syringe has a barrel member 13 and a plunger element 14. The syringe includes a male needle mounting means 15 having a conical surface 16 that is normally adapted to mate with a mounting means on a needle such as needle 12. Conical surface 16 terminates in opening 17. Filter 11 includes an elongate tubular body 18 having a first mounting means 19 of outwardly tapered concial configuration adapted to mate with conical surface 16 of syringe 10 in a fluid sealing manner. At the opposite end of elongate tubular body 18 there is a second mounting means 20 of inwardly tapered conical configuration adapted to mate with corresponding mounting means of a needle such as needle 12.

Needle 12 includes an outwardly tapered female mounting means 21 of conical configuration and cannula 22.

Mounted inside elongate tubular body 18 are elongate microporous hollow filter fibres 23. As best shown in FIG. 2, hollow fibres 23 have an open end 24 and a closed end 25. While a single fibre can be used having an open end and a sealed closed end, the arrangement shown in FIG. 2 wherein a fibre is looped back upon itself to form two open ends 24, with the loop providing closed ends 25, is preferred.

Flow blocking material 26 is arranged to position hollow filtering fibres 23 in elongate tubular body 18 such that flow through tubular body 18 other than through the material of hollow filtering fibres 23 is blocked. It is preferred to have the blocking material 26 in this position to provide a reservoir of fluid upstream of said material in said elongate tubular body 18 to promote transverse flow of said fluid material through the material of hollow filter fibres 23.

In a preferred form of the invention, the concial surfaces of elements 16, 19, 20 and 21 all have a conical angle of from about 1' to about 2'.

The elongate tubular body 18 of filter 11, in its referred form, should not exceed the diameter of a barrel member 13 of syringe 10.

In a preferred form, the total length of filter unit 11 will be about 0.5 inches to about 4 inches with a preferred outside diameter in the range of about 0.10 inches to about 0.30 inches with an inside diameter approximating about 0.05 inches to about 0.20 inches. The ratio of length to the outside diameter of filter will be in the range of about 2 to about 20.

The microporous hollow fibres 23 can be of any length, preferably up to and including the length of tubular body 18 less the depth of protrustion of the male needle mounting means 15 which otherwise might damage the fibres. The fibres 23 can also be relatively short in length compared to the length of tubular body 18 provided that sufficient filtration surface is present for the particular application.

The porosity rating of fibres 23 is in the microporous range of about 0.05 to about 1 microns. A preferred range is about 0.1 to about 0.45 microns.

The inside diameter for fibres 23 can be from about 0.008 inches to about 0.08 inches with a preferred inside diameter being in the range of about 0.012 inches to about 0.05 inches with a further preferred diameter being about 0.18 10%. It has been found in accordance with the invention that larger fibres under the pressures applied by injection force on the syringe may collapse. Smaller diameter fibres also increase the packing density. The outside diameter should be that which will result in a wall thickness of about 0.001 inches to about 0.005 inches with a preferred wall thickness being about 0.0015 inches to about 0.004 inches.

Flow blocking potting material 26 can be selected from the group consisting of silicone, polyurethane, epoxy, and cyanoacrylate ester resins with polyurethane being the currently preferred potting material. Elongate tubular body 18 in its preferred form is made out of a rigid plastic material, preferably transparent or transluscent, such as an acrylic or polycarbonate resin.

The effective filtration area of the microporous hollow fibres 23 in a given filter element 11 is in the range of about 0.25 cm$^2$ to about 10 cm$^2$ with a preferred range being about 5.0 cm$^2$ or less. The effective filtration area is measured on the inside walls of the fibres.

The porosity of fibres 23 should be greater than about 50% with a preferred range being about 65% to 85% with the upper range of porosity being limited at a point where the fibres have no structural integrity.

Packing density of fibres 23 in tubular body 18 as expressed in a ratio of cross-sectional areas of fibres to cross-sectional area of the lumen of tubular body 18 should be less than about 60%. The number of fibres 23 in tubular body 18 is preferably between 1 and 10 and more preferably between 2 and 8.

Figure 4:
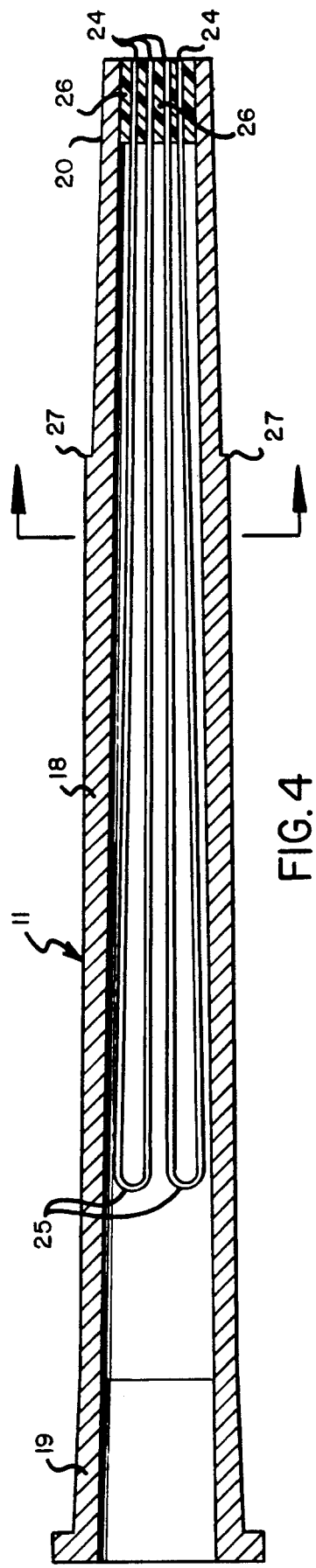
FIG. 4 is a view similar to FIG. 2 showing an alternate embodiment of the invention; and, FIG. 5 is a view in cross-section taken on lines 5—5 of FIG. 4.

In FIG. 4, there is shown an alternate embodiment according to the invention wherein the elongate tubular body is tapered, in this case, at an angle of about 1' to about 3' and wherein there are also included finger grippable projections in the form of an elongate ribs 27. These ribs extending substantially the length of the tubular portion 18 of filter unit 11. The existence of ribs 27 make it not only easier to grip the filter when it is connected with needle 12 and syringe 10, but further make it easier to install on the syringe and to facilitate removal and connection with needle 12.

An added advantage of the elongate filter 18 of the invention is that the filter itself will fit into ampoules for the withdrawal of liquids therefrom. The filter, therefore, has the advantage of filtering either in asperation or injection of fluids.

Figure 5:
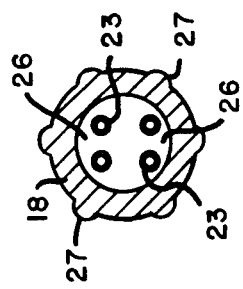

As best shown in FIG. 5, grips 27 can be spaced equal distance around tubular body 18 and it is preferred to have such ribs projecting from said tubular body at a distance in the range of from 0.008 to 0.015 inches. The elongate ribs 27 are themselves tapered and it is preferred that the angle of taper be from about 1.0 to about 1.5 degrees. The taper of the tube 18 and the ribs 27 facilitate manufacture of the filter by the injection molding process whereby the parting line can be at the face 28 of a standard luer fitting 29. It is also preferred, to have the interior of tube 18 tapered at an angle substantially the same as that of the exterior to provide for easy removal from mold parts in the injection molding process.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

I claim What is claimed is:

1. A filtering device, adapted to be used with a syringe and a needle, for filtering fluids drawn in or ejected from said syringe, said filtering device comprising:

(a) An elongate tubular body having a first mounting means on one end thereof adapted to be sealingly connected to the needle mounting on said syringe and a second mounting means on the opposite end thereof adapted to be sealingly connected to the cooperative syringe mounting means on said needle;

(b) Elongate microporous hollow filter fibres arranged longitudinally within said tubular body, said fibres being closed at one end thereof and open at the opposite end thereof; and, (c) Flow blocking material arranged around said fibres for blocking flow through said tubular body other than through the material of said hollow fibres, said flow blocking material being provided at a position in said elongate tubular body to provide with said elongate microporous hollow filter fibres a reservoir of fluid around said hollow filter fibres to promote transverse flow of said fluid through the material of said hollow filter fibers, (d) Said first mounting means being adapted to be connected to a male needle mounting means of conical configuration of a syringe and said second mounting means being adapted to be sealingly connected to a female mounting means of conical configuration of a needle, said first and second mounting means being conical in configuration and adapted to mate with corresponding conical portions of said needle mounting means and said needle, the conical angle of said concial mounting being about 1' to 2', said flow blocking material being located in said tubular body adjacent the end of said tubular body having said second mounting means, the open end of said elongate microporous hollow fibres being adjacent the end of said tubular body having said second mounting means, the ratio of length to the outside diameter of said elongate tubular body being in the range of about 5 to 20, the porosity rating of said fibres being in the range of about 0.05 to about 1 micron and the packing density of said fibres being less than about 60%, the porosity of said fibres being greater than about 50%, the effective filtering area of said fibres being about 1 cm to about 10 cm the total length of said filtering device beinb about 0.5 inches to about 4 inches, the outside diameter of said elongate tubular body being about 0.10 inches to about 0.30 inches and, the inside diameter of said elongate tubular body being about 0.05 inch to about 0.20 inches.

2. A combination syringe, filter and needle comprising:
(1) a syringe having a mounting means thereon;
(2) a needle having a mounting means thereon;
(3) a filter for filtering fluids drawn in or ejected from said syringe, said filter comprising:
  (a) an elongate tubular body having a first mounting means on one end thereof adapted to be sealingly connected to the needle mounting on said syringe and a second mounting means onthe opposite end thereof adapted to be sealingly connected to the cooperative syringe mounting means on said needle;
  (b) elongate microporous hollow filter fibres arranged longitudinally within said tubular body, said fibres being closed at one end thereof and open at the opposite end thereof; and,
  (c) flow blocking material arranged around said fibres for blocking flow through said tubular body other than through the material of said hollow fibres, said flow blocking material being provided at a position in said elongate tubular body to provide with said elongate microporous hollow filter fibres a reservoir of fluid around said hollow filter fibres to promote transverse flow of said fluid through the material of said hollow filter fibers,
  (d) said first mounting means being adapted to be connected to a male needle mounting means of conical configuration of a syringe and said second mounting means being adapted to be sealingly connected to a female mounting means of conical configuration of a needle, said first and second mounting means being conical in configuration and adapted to mate with corresponding conical portions of said needle mounting means and said needle, the conical angle of said conical mounting being about 1' to 2', said flow blocking material being located in said tubular body adjacent the end of said tubular body having said second mounting means, the open end of said elongate microporous hollow fibres being adjacent the end of said tubular body having said second mounting means, the ration of length to the outside diameter of said elongate tubular body being in the range of about 5 to 20, the porosity rating of said fibres being in the range of about 0.05 to about 1 micron and the packing density of said fibres being less than about 60%, the porosity of said fibres being greater than about 50%, the effective filtering area of said fibres being about 1 cm to about 10 cm the total length of said filtering device being about 0.5 inches to about 4 inches, the outside diameter of said elongate tubular body being about 0.10 inches to about 0.30 inches and, the inside diameter of aid elognate tubular body being about 0.05 inch to about 0.20 inches.

* * * * *